US007338285B1

United States Patent
Balaban

(10) Patent No.: US 7,338,285 B1
(45) Date of Patent: Mar. 4, 2008

(54) DISPOSABLE PROPHY ANGLE WITH ENCOMPASSING INTEGRAL TOROIDAL PASTE POUCH FOR ATTACHING TO A DENTAL HANDPIECE

(76) Inventor: Elena Balaban, 45-41 39th Pl., Apt. 1B, Long Island City, NY (US) 11104-3500

(*) Notice: Subject to any disclaimer, the term of this patent is extended or adjusted under 35 U.S.C. 154(b) by 0 days.

(21) Appl. No.: 11/508,368

(22) Filed: Aug. 23, 2006

(51) Int. Cl.
A61C 1/10 (2006.01)
A61C 3/08 (2006.01)
A61C 3/02 (2006.01)
A61C 13/24 (2006.01)

(52) U.S. Cl. .......... 433/125; 433/82; 433/83; 433/144; 433/183; 433/184; 433/185; 433/186

(58) Field of Classification Search .......... 433/82, 433/83, 125, 140, 144, 183–186
See application file for complete search history.

(56) References Cited

U.S. PATENT DOCUMENTS

| 2,738,528 A | * | 3/1956 | Fridge, Sr. .......... 15/97.1 |
| 3,691,636 A | | 9/1972 | Deuschle |
| 5,642,994 A | * | 7/1997 | Chipian et al. .......... 433/82 |
| 5,871,353 A | | 2/1999 | Pierce et al. |
| 6,095,813 A | | 8/2000 | Broyles |
| 6,164,967 A | | 12/2000 | Sale et al. |
| 6,632,090 B1 | | 10/2003 | Randolph |

* cited by examiner

Primary Examiner—Samchuan C. Yao
Assistant Examiner—Yogesh P Patel
(74) Attorney, Agent, or Firm—Richard L. Miller

(57) ABSTRACT

A dental cleaning attachment for a dental handpiece which comprises a disposable prophy angle having a neck and a right angle head, wherein the neck is removably attached to the dental handpiece. A polishing cup is rotatably connected to the head of the prophy angle. An encompassing toroidal pouch has a tube fluidly formed to and extending from the toroidal pouch. The tube runs externally along a top surface of the neck, is bent at a right angle, goes through a rear aperture in the head of the prophy angle and into a top aperture in the polishing cup. A paste material is carried within the toroidal pouch, the tube and the polishing cup. When the dental handpiece is gripped by a hand of a dental hygienist and the polishing cup is applied to a tooth, any finger of the hand of the dental hygienist can squeeze the toroidal pouch to force some of the paste material through the tube and out of the polishing cup, so that the paste material can be applied onto the tooth for cleaning.

7 Claims, 2 Drawing Sheets

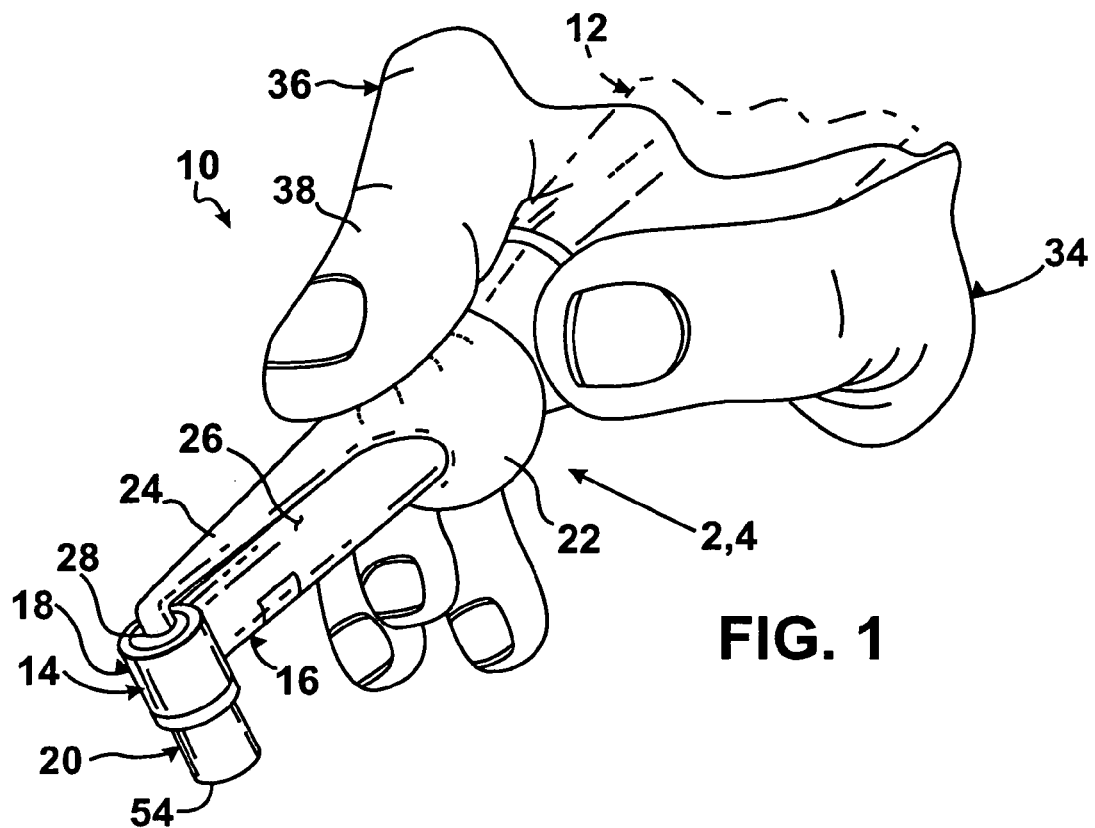
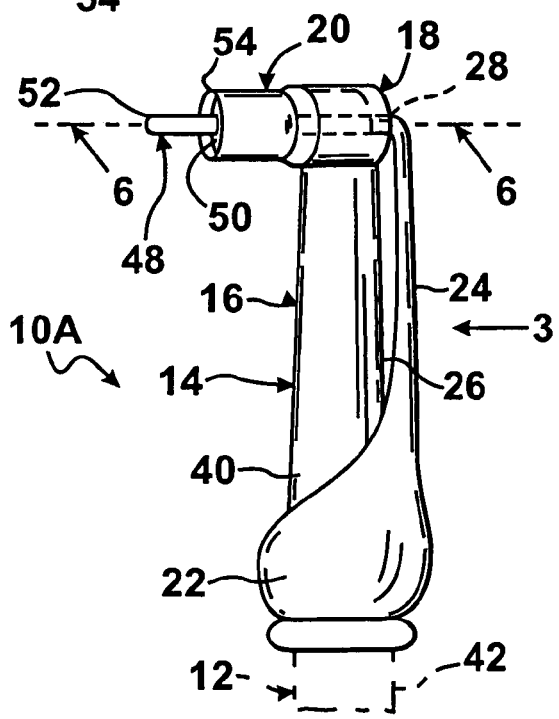
FIG. 2
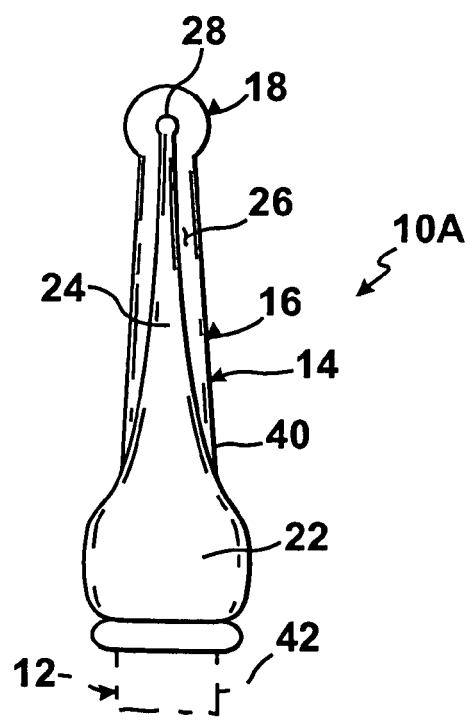
FIG. 3

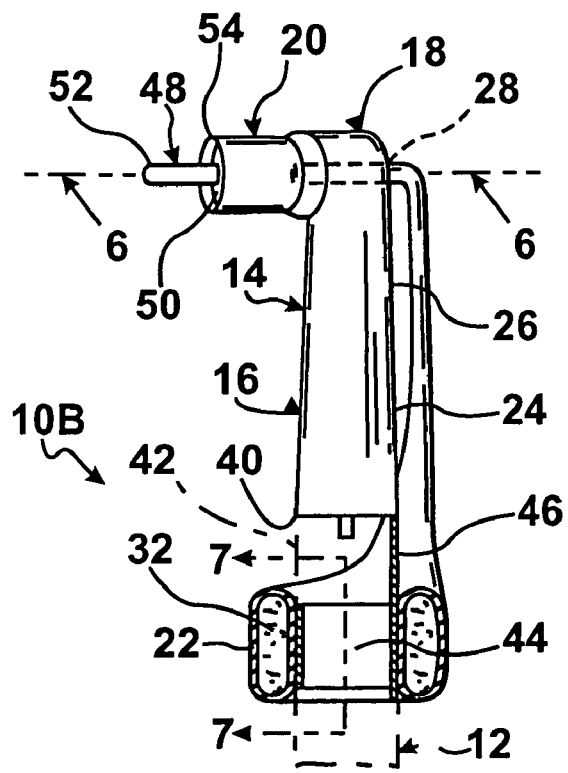
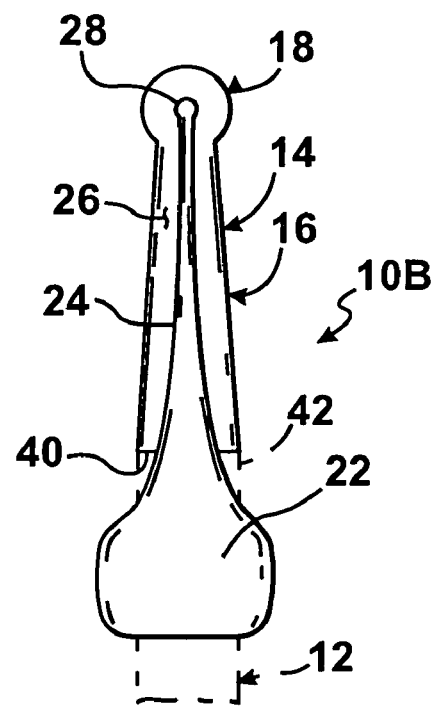
FIG. 4
FIG. 5
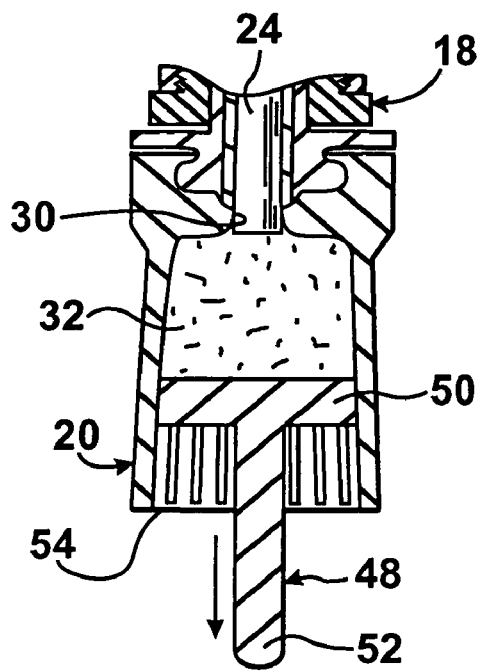
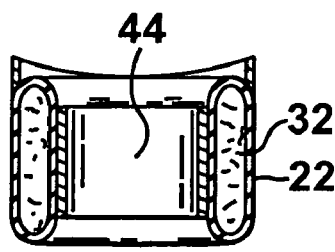
FIG. 6
FIG. 7

DISPOSABLE PROPHY ANGLE WITH ENCOMPASSING INTEGRAL TOROIDAL PASTE POUCH FOR ATTACHING TO A DENTAL HANDPIECE

BACKGROUND OF THE INVENTION

1. Field of the Invention

The presented invention relates to a dental cleaning device, and more particularly, a disposable prophy angle with encompassing integral toroidal paste pouch which attaches to a dental handpiece.

2. Description of the Prior Art

Numerous innovations for teeth polishing equipment have been provided in the prior art that will be described. Even though these innovations may be suitable for the specific individual purposes to which they address, however, they differ from the presented invention.

A FIRST EXAMPLE, U.S. Pat. No. 3,691,636 issued on Sep. 19, 1972 to Deuschle teaches a dental prophylactic device, commonly known as a prophy angle dental handpiece, for use by a dentist in cleaning a patient's teeth. The prophy angle herein comprises a disposable prophylactic dental handpiece containing a supply of abrasive paste and suitable means for delivering the paste progressively to a polishing cup projecting at right angles from the generally cylindrical body of the prophy angle.

A SECOND EXAMPLE, U.S. Pat. No. 5,642,994 issued on Jul. 1, 1997 to Chipian, et al. teaches a fluid storage and dispensing container for cleaning teeth, which includes a modified prophy angle headpiece that attaches to existing hand-held prophy cup dental instrument handpieces. The headpiece has an integrated passage through the headpiece by which a fluid is dispensed from the fluid container to the rotatable prophy cup. The headpiece has a lumen through the angle that won't tear or close under flow pressure. The headpiece has a shelf on a top surface for guiding placement of the fluid container, and a snap-fit retaining clip at a base of the headpiece for securing a plurality of different fluid containers. A preferred embodiment of a fluid storage container is a flexible tube that is depressed by a finger or thumb to dispense a fluid such as prophylactic paste or a polishing lubricant to the prophy cup.

A THIRD EXAMPLE, U.S. Pat. No. 5,871,353 issued on Feb. 16, 1999 to Pierce, et al. teaches an invention that provides for the incorporation of dentifrice preparations, which are commonly accessed from a container on a tray during teeth cleaning, internally within the housing of a disposable prophy angle. Auger, baffle or piston members are used to move the preparations from the housing through passages in the head of the prophy angle to a moving prophy cup. If a reusable autoclavable prophy angle is being used, the invention provides for an annular chamber containing the dentifrice preparation that interfits as a sleeve over the prophy angle body. In such case, the prophy angle head is enlarged and includes an inlet connection with the annular chamber. Passageways in the head direct the dentifrice preparation to the prophy cup and a piston ring is used to move the dentifrice preparation from the chamber through the passageways. Alternatively, an external pressurized supply of the dentifrice preparation may be connected to a conduit which is attached to the body in place of the annular chamber. The conduit interconnects the external supply with the enlarged head inlet for providing dentifrice preparation to the prophy cup. In all cases, the prophy cup may include a one-way valve to prevent backflow of unwanted materials.

A FOURTH EXAMPLE, U.S. Pat. No. 6,095,813 issued on Aug. 1, 2000 to Broyles teaches a method of applying a dental composition to tooth structure of a dental patient that includes the act of providing an applicator having an empty chamber at least partially surrounded by flexible wall portions. A tip portion of the applicator is placed into a bulk container having a quantity of dental composition, and the wall portions are squeezed together. When the wall portions are released, a portion of the dental composition is drawn into the chamber by suction. The wall portions are then squeezed together once the tip portion of the applicator has been placed next to tooth structure of a dental patient in order to dispense at least a portion of the dental composition directly onto the tooth structure. Since a sufficient amount of composition is drawn from the bulk container before the applicator is placed in the patient's oral cavity, the likelihood of cross-contamination between dental patients is substantially reduced.

A FIFTH EXAMPLE, U.S. Pat. No. 6,164,967 Issued on Dec. 26, 2000 to Sal, et al. teaches a fluid delivery powered toothbrush that utilizes a removable/disposable neck assembly that contains a fluid reservoir, a fluid delivery system and a fluid path therein leading to a brush receptacle. No fluid is used in or passes through the toothbrush handle. Preferably a pump is located in the neck assembly and activated at the same time as the brush drive such that fluid is delivered during brushing. In one embodiment of the invention, the brush is replaced with a nozzle for providing fluid prior to or after brushing. The components for the neck assembly are disposable to minimize cross-contamination while enhancing fluid delivery to the teeth during brushing.

A SIXTH EXAMPLE, U.S. Pat. No. 6,632,090 issued on Oct. 14, 2003 to Randolph teaches a system and method for dispensing prophylaxis paste during dental cleaning procedures which includes a flow control valve, which is actuated by pressure between the prophy cup and the tooth, and also includes a source of prophylaxis paste delivered under pressure It is apparent now that numerous innovations for teeth polishing equipment have been provided in the prior art that are adequate for various purposes. Furthermore, even though these innovations may be suitable for the specific individual purposes to which they address, accordingly, they would not be suitable for the purposes of the invention as heretofore described.

SUMMARY OF THE INVENTION

AN OBJECT of the presented invention is to provide a disposable prophy angle with encompassing integral toroidal paste pouch which attaches to a dental handpiece that avoids the disadvantages of the prior art.

ANOTHER OBJECT of the presented invention is to provide a disposable prophy angle with encompassing integral toroidal paste pouch which attaches to a dental handpiece that is simple and inexpensive to manufacture.

STILL ANOTHER OBJECT of the presented invention is to provide a disposable prophy angle with encompassing integral toroidal paste pouch which attaches to a dental handpiece that is simple to use.

BRIEFLY STATED, STILL YET ANOTHER OBJECT of the presented invention is to provide a disposable prophy angle with encompassing integral toroidal paste pouch which attaches to a dental handpiece that is a dental cleaning attachment for a dental handpiece which comprises a disposable prophy angle having a neck and a right angle head, wherein the neck is removably attached to the dental handpiece. A polishing cup is rotatably connected to the head of the prophy angle. An encompassing toroidal pouch has a tube fluidly formed to and extending from the toroidal pouch. The tube runs externally along a top surface of the neck, is bent at a right angle, goes through a rear aperture in the head of the prophy angle and into a top aperture in the polishing cup. A paste material is carried within the toroidal pouch, the tube and the polishing cup. When the dental handpiece is gripped by a hand of a dental hygienist and the polishing cup is applied to a tooth, any finger of the hand of the dental hygienist can squeeze the toroidal pouch to force some of the paste material through the tube and out of the polishing cup, so that the paste material can be applied onto the tooth for cleaning.

The novel features which are considered characteristic of the presented invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWINGS

The figures of the drawings are briefly described as follows:

FIG. 1 is a diagrammatic perspective view showing an embodiment of the invention held by a dental technician ready for use;

FIG. 2 is a diagrammatic side perspective view, taken in the direction of arrow 2 in FIG. 1, of a first embodiment of the invention, showing the removable paste plug within the polishing cup;

FIG. 3 is a diagrammatic top elevational view, taken in the direction of arrow 3 in FIG. 2;

FIG. 4 is a diagrammatic side perspective view, with parts broken away and in section, taken in the direction of arrow 4 in FIG. 1, of a second embodiment of the invention, showing the removable paste plug within the polishing cup;

FIG. 5 is a diagrammatic top elevational view, taken in the direction of arrow 5 in FIG. 4;

FIG. 6 is an enlarged diagrammatic cross sectional view, with parts broken away, taken on line 6-6 in FIGS. 2 and 4 showing the removable paste plug within the polishing cup in greater detail; and FIG. 7 is an enlarged diagrammatic cross sectional view taken on line 7-7 in FIG. 4 showing the structure of the toroidal paste pouch and ring in greater detail.

| A MARSHALLING OF REFERENCE NUMERALS UTILIZED IN THE DRAWING | |
|---|---|
| 10 | dental cleaning attachment |
| 10A | first dental cleaning attachment |
| 10B | second dental cleaning attachment |
| 12 | dental handpiece |
| 14 | disposable prophy angle of dental cleaning attachment 10 |
| 16 | neck of prophy angle 14 |
| 18 | right angle head of prophy angle 14 |
| 20 | polishing cup of dental cleaning attachment 10 |
| 22 | toroidal pouch of dental cleaning attachment 10 |
| 24 | tube of toroidal pouch |
| 26 | top surface of neck 16 |
| 28 | rear aperture in head 18 |
| 30 | top aperture in polishing cup 20 |
| 32 | paste material of dental cleaning attachment 10 |
| 34 | hand of dental hygienist 36 |
| 36 | dental hygienist |
| 38 | finger of hand 34 |
| 40 | bottom end of neck 16 |
| 42 | forward end of dental handpiece 12 |
| 44 | ring in toroidal pouch 22 |
| 46 | upwardly projecting arm of ring 44 |
| 48 | removable paste plug in polishing cup 20 |
| 50 | disc member of paste plug 48 |
| 52 | shaft of paste plug 48 |
| 54 | bottom end of polishing cup 20 |

DETAILED DESCRIPTION OF THE PREFERRED EMBODIMENT

Referring now to the figures, in which like numerals indicate like parts, and particularly to FIG. 1, which is a diagrammatic perspective view showing an embodiment of the invention held by a dental technician ready for use, and as such, will be discussed with reference thereto.

An embodiment of the invention is a dental cleaning attachment 10 for a dental handpiece 12 which comprises a disposable prophy angle 14 having a neck 16 and a right angle head 18, wherein the neck 16 is removably attached to the dental handpiece 12. A polishing cup 20 is rotatably connected to the head 18 of the prophy angle 14. An encompassing toroidal pouch 22 has a tube 24 fluidly formed to and extends from the toroidal pouch 22. The tube 24 runs externally along a top surface 26 of the neck 16, is bent at a right angle, goes through a rear aperture 28 in the head 18 of the prophy angle 14 and into a top aperture 30 in the polishing cup 20 (see FIG. 6). A paste material 32, as shown in FIG. 6 is carried within the toroidal pouch 22, the tube 24 and the polishing cup 20. When the dental handpiece 12 is gripped by a hand 34 of a dental hygienist 36 and the polishing cup 20 is applied to a tooth (not shown), any finger 38 of the hand 34 of the dental hygienist 36 can squeeze the toroidal pouch 22 to force some of the paste material 32 through the tube 24 and out of the polishing cup 20, so that the paste material 32 can be applied onto the tooth for cleaning. This arrangement of having the toroidal pouch 22 encompass the bottom end of neck 16 allows the dental hygienist 36 to squeeze the toroidal pouch 22 regardless of the orientation the polishing cup 20 with respect the hand 34 of the dental hygienist 36.

FIG. 2 is a diagrammatic side perspective view, taken in the direction of arrow 2 in FIG. 1, of a first embodiment of the invention, showing a removable paste plug within the polishing cup, while FIG. 3 is a diagrammatic top elevational view, taken in the direction of arrow 3 in FIG. 2, and as such, will be discussed with reference thereto.

The dental cleaning attachment 10A comprises the encompassing toroidal pouch 22 extending about a bottom end 40 of the neck 16 of the prophy angle 14. The bottom end 40 of the neck 16 of the prophy angle 14 is removably attached to a forward end 42 of the dental handpiece 12.

FIG. 4 is a diagrammatic side perspective view, with parts broken away and in section, taken in the direction of arrow 4 in FIG. 1, of a second embodiment of the invention, showing the removable paste plug within the polishing cup. FIG. 5 is a diagrammatic top elevational view, taken in the direction of arrow 5 in FIG. 4, while FIG. 7 is an enlarge diagrammatic cross sectional view taken on line 7-7 in FIG. 4 showing the structure of the toroidal paste pouch and ring in greater detail, and as such, will be discussed with reference thereto.

The dental cleaning attachment 10B comprises a ring 44 having an upwardly projecting arm 46 integral with the top surface 26 of the neck 16 of the prophy angle 14. The encompassing toroidal pouch 22 extends about the ring 44, while the ring 44 fits over the dental handpiece 12 when a bottom end 40 of the neck 16 of the prophy angle 14 is removably attached to a forward end 42 of the dental handpiece 12.

FIG. 6 is an enlarged diagrammatic cross sectional view, with parts broken away, taken on line 6-6 in FIGS. 2 and 4 showing the removable paste plug within the polishing cup in greater detail, and as such, will be discussed with reference thereto.

A removable paste plug 48 is in the polishing cup 20, wherein the paste plug 48 seals the paste material 32 within the polishing cup 20 before being used. The paste plug 48 comprises a disc member 50 which fits within the polishing cup 20. A shaft 52 is integral with and extends from center of the disc member 50. The shaft 52 projects outwardly from bottom end 54 of the polishing cup 20 to be grasped and pulled out to remove the disc member 50 from the polishing cup 20 to release the paste material 32 therein.

It will be understood that each of the elements described above, or two or more together, may also find a useful application in other types of constructions differing from the types described above.

While the invention has been illustrated and described as embodiments of a disposable prophy angle with encompassing integral toroidal paste pouch which attaches to a dental handpiece, accordingly it is not limited to the details shown, since it will be understood that various omissions, modifications, substitutions and changes in the forms and details of the device illustrated and its operation can be made by those skilled in the art without departing in any way from the spirit of the invention.

Without further analysis, the foregoing will so fully reveal the gist of the invention that others can, by applying current knowledge, readily adapt it for various applications without omitting features that, from the standpoint of prior art, fairly constitute characteristics of the generic or specific aspects of this invention.

The invention claimed is:

1. A dental cleaning attachment for a dental handpiece which comprises:
    a) a disposable prophy angle having a neck and a right angle head, wherein said neck is removably attached to the dental handpiece;
    b) a polishing cup rotatably connected to said head of said prophy angle;
    c) an encompassing toroidal pouch having a tube fluidly formed to and extending from said toroidal pouch, wherein said tube runs externally along a top surface of said neck, is bent at a right angle, goes through a rear aperture in said head of said prophy angle and into a top aperture in said polishing cup; and
    d) a paste material carried within said toroidal pouch said tube and said polishing cup, wherein when the dental handpiece is gripped by a hand of a dental hygienist and said polishing cup is applied to a tooth, any finger of the hand of the dental hygienist can squeeze said toroidal pouch to force some of said paste material through said tube and out of said polishing cup, so that said paste material can be applied onto the tooth for cleaning.

2. The dental cleaning attachment as recited in claim 1, further comprising said encompassing toroidal pouch extending about a bottom end of said neck of said prophy angle, wherein said bottom end of said neck of said prophy angle is removably attached to a forward end of the dental handpiece.

3. The dental cleaning attachment as recited in claim 2, further comprising a removable paste plug in said polishing cup, wherein said paste plug seals said paste material within said polishing cup before being used.

4. The dental cleaning attachment as recited in claim 3, wherein said paste plug comprises:
    a) a disc member which fits within said polishing cup; and
    b) a shaft integral with and extending from center of said disc member, wherein said shaft projects outwardly from bottom end of said polishing cup to be grasped and pulled out to remove said disc member from said polishing cup to release said paste material therein.

5. The dental cleaning attachment as recited in claim 1, further comprising a ring having an upwardly projecting arm integral with said top surface of said neck of said prophy angle, wherein said encompassing toroidal pouch extends about said ring, while said ring fits over the dental handpiece when a bottom end of said neck of said prophy angle is removably attached to a forward end of the dental handpiece.

6. The dental cleaning attachment as recited in claim 5, further comprising a removable paste plug in said polishing cup, wherein said paste plug seals said paste material within said polishing cup before being used.

7. The dental cleaning attachment as recited in claim 6, wherein said paste plug comprises:
    a) a disc member which fits within said polishing cup; and
    b) a shaft integral with and extending from center of said disc member, wherein said shaft projects outwardly from bottom end of said polishing cup to be grasped and pulled out to remove said disc member from said polishing cup to release said paste material therein.

* * * * *